(12) United States Patent
Donadio, III et al.

(10) Patent No.: US 10,835,366 B2
(45) Date of Patent: Nov. 17, 2020

(54) ARTERIAL AND VENOUS ANCHOR DEVICES FORMING AN ANASTOMOTIC CONNECTOR AND SYSTEM FOR DELIVERY

(71) Applicant: PHRAXIS, INC., St. Paul, MN (US)

(72) Inventors: James V. Donadio, III, Carver, MN (US); Steven E. Scott, Excelsior, MN (US); Alexander S. Yevzlin, Black Earth, WI (US); Robert Ziebol, Blaine, MN (US); Reed A. Houge, Flagstaff, AZ (US); Doug S. Wahnschaffe, Rogers, MN (US); Steve Berhow, Rogers, MN (US); Jeff M. Welch, Maple Grove, MN (US)

(73) Assignee: PHRAXIS INC., St. Paul, MN (US)

( * ) Notice: Subject to any disclaimer, the term of this patent is extended or adjusted under 35 U.S.C. 154(b) by 559 days.

(21) Appl. No.: 14/405,088

(22) PCT Filed: Dec. 3, 2012

(86) PCT No.: PCT/US2012/067561
§ 371 (c)(1),
(2) Date: Dec. 2, 2014

(87) PCT Pub. No.: WO2013/187927
PCT Pub. Date: Dec. 19, 2013

(65) Prior Publication Data
US 2015/0134051 A1    May 14, 2015

Related U.S. Application Data

(60) Provisional application No. 61/683,898, filed on Aug. 16, 2012.

(51) Int. Cl.
*A61F 2/06* (2013.01)
*A61B 17/11* (2006.01)
(Continued)

(52) U.S. Cl.
CPC .............. *A61F 2/064* (2013.01); *A61B 17/11* (2013.01); *A61F 2/07* (2013.01); *A61F 2/848* (2013.01);
(Continued)

(58) Field of Classification Search
CPC . A61B 17/11; A61B 17/1114; A61B 17/1128; A61B 2017/1103;
(Continued)

(56) References Cited

U.S. PATENT DOCUMENTS

| 3,818,511 A | 6/1974 | Goldberg et al. |
| 4,352,358 A | 10/1982 | Angelchik |

(Continued)

FOREIGN PATENT DOCUMENTS

| CA | 2366703 A1 | 9/2000 |
| CA | 2574941 A1 | 7/2007 |

(Continued)

OTHER PUBLICATIONS

Japanese Office Action issued by the Japanese Patent Office (translated), regarding corresponding patent application Serial No. 2014-516024, dated Oct. 15, 2014; 5 pages.

(Continued)

*Primary Examiner* — Katherine H Schwiker
(74) *Attorney, Agent, or Firm* — Fox Rothschild LLP

(57) ABSTRACT

An arterial anchor device and a venous anchor device operably coupled by graft material to form an anastomotic convector is provided. The arterial anchor device comprises a generally tubular main body including a distal end and a proximal end, the distal end defining a plurality of flanges integrally formed with the tubular main body and being movable from a first loaded position to a second expanded position. The venous anchor device includes a tubular main body having a metal frame structure and including a distal (Continued)

end and a proximal end, the distal end including a plurality of barbs thereon wherein said distal end has an outer diameter greater than the proximal end. The arterial anchor device and venous devices are fluidly connected by a graft to form an anastomotic connector.

20 Claims, 15 Drawing Sheets

(51) Int. Cl.
  A61F 2/958 (2013.01)
  A61F 2/966 (2013.01)
  A61F 2/07 (2013.01)
  A61M 1/36 (2006.01)
  A61F 2/848 (2013.01)
  A61F 2/915 (2013.01)
  A61B 17/00 (2006.01)
  A61F 2/91 (2013.01)

(52) U.S. Cl.
  CPC ............ A61F 2/915 (2013.01); A61F 2/958 (2013.01); A61F 2/966 (2013.01); A61M 1/3655 (2013.01); A61B 2017/00526 (2013.01); A61B 2017/00867 (2013.01); A61B 2017/1107 (2013.01); A61B 2017/1135 (2013.01); A61F 2/91 (2013.01); A61F 2002/067 (2013.01); A61F 2002/068 (2013.01); A61F 2002/91525 (2013.01); A61F 2002/91558 (2013.01); A61F 2002/91583 (2013.01); A61F 2210/0014 (2013.01); A61F 2250/0039 (2013.01); A61F 2250/0069 (2013.01); F04C 2270/041 (2013.01)

(58) Field of Classification Search
  CPC ....... A61B 2017/1107; A61B 2017/111; A61B 2017/1117; A61B 2017/1121; A61B 2017/1132; A61B 17/1146; A61B 2017/1135; A61B 2017/1139; A61B 17/115; A61B 17/1152; A61B 17/1155; A61B 17/1157; A61B 2017/1142; A61F 2002/061; A61F 2002/065; A61F 2002/067; A61F 2002/068; A61F 2002/072; A61F 2002/075; A61F 2002/077; A61F 2/82; A61F 2/86; A61F 2002/821; A61F 2002/823; A61F 2002/825; A61F 2002/826; A61F 2002/828; A61F 2/06; A61F 2/062; A61F 2/064; A61F 2/07; A71B 2017/1135; A71B 2017/1139; A61M 1/3655; A61M 1/3653
  See application file for complete search history.

(56) References Cited

U.S. PATENT DOCUMENTS

| | | |
|---|---|---|
| 4,368,736 A | 1/1983 | Kaster |
| 4,512,761 A | 4/1985 | Raible |
| 5,383,892 A * | 1/1995 | Cardon ................ A61F 2/90 606/198 |
| 5,456,712 A | 10/1995 | Maginot |
| 5,755,775 A | 5/1998 | Trerotola |
| 5,755,778 A | 5/1998 | Kleshinski |
| 5,968,089 A | 10/1999 | Krajicek |
| 5,972,017 A | 10/1999 | Berg et al. |
| 5,989,276 A * | 11/1999 | Houser ................ A61B 17/11 606/139 |
| 6,030,392 A | 2/2000 | Dakov |
| 6,030,395 A | 2/2000 | Nash et al. |
| 6,179,848 B1 | 1/2001 | Solem |
| 6,190,590 B1 | 2/2001 | Randall et al. |
| 6,210,429 B1 | 4/2001 | Vardi et al. |
| 6,241,743 B1 | 6/2001 | Levin et al. |
| 6,241,757 B1 * | 6/2001 | An ........................ A61F 2/90 623/1.1 |
| 6,270,524 B1 | 8/2001 | Kim |
| 6,277,133 B1 | 8/2001 | Kanesaka |
| 6,293,955 B1 | 9/2001 | Houser et al. |
| 6,402,767 B1 | 6/2002 | Nash et al. |
| 6,406,488 B1 * | 6/2002 | Tweden ................ A61F 2/06 623/1.16 |
| 6,419,681 B1 | 7/2002 | Vargas et al. |
| 6,451,048 B1 | 9/2002 | Berg et al. |
| 6,458,140 B2 | 10/2002 | Akin et al. |
| 6,464,665 B1 | 10/2002 | Heuser |
| 6,464,709 B1 | 10/2002 | Shennib et al. |
| 6,482,214 B1 | 11/2002 | Sidor et al. |
| 6,485,513 B1 | 11/2002 | Fan |
| 6,517,558 B2 | 2/2003 | Gittings et al. |
| 6,582,463 B1 | 6/2003 | Mowry et al. |
| 6,585,760 B1 | 7/2003 | Fogarty |
| 6,599,303 B1 | 7/2003 | Peterson et al. |
| 6,648,901 B2 | 11/2003 | Fleischman et al. |
| 6,682,540 B1 | 1/2004 | Sancoff et al. |
| 6,719,781 B1 | 4/2004 | Kim |
| 6,743,243 B1 | 6/2004 | Roy et al. |
| 6,855,162 B2 | 2/2005 | Parodi |
| 7,025,773 B2 | 4/2006 | Gittings et al. |
| 7,056,326 B2 | 6/2006 | Bolduc et al. |
| 7,105,020 B2 | 9/2006 | Greenberg et al. |
| 7,175,652 B2 | 2/2007 | Cook et al. |
| 7,267,680 B2 | 9/2007 | Wright |
| 7,591,827 B2 | 9/2009 | Hill et al. |
| 7,611,523 B2 | 11/2009 | Vargas et al. |
| 7,691,140 B2 | 4/2010 | Bates et al. |
| 7,722,665 B2 | 5/2010 | Anwar et al. |
| 7,766,955 B2 | 8/2010 | Vardi et al. |
| 7,828,834 B2 | 11/2010 | Garbe |
| 7,850,725 B2 | 12/2010 | Vardi et al. |
| 7,892,247 B2 | 2/2011 | Conston et al. |
| 7,927,343 B2 | 4/2011 | Hill et al. |
| 8,287,586 B2 | 10/2012 | Schaeffer et al. |
| 8,298,251 B2 | 10/2012 | Golden et al. |
| 8,343,204 B2 | 1/2013 | Osborne |
| 8,361,092 B1 | 1/2013 | Asfora |
| 8,366,651 B2 | 2/2013 | Dakin et al. |
| 8,439,963 B2 | 5/2013 | Dickinson et al. |
| 8,486,153 B2 | 7/2013 | Levine et al. |
| 8,551,127 B2 | 10/2013 | Asfora et al. |
| 8,628,583 B2 | 1/2014 | Meade et al. |
| 8,715,336 B2 | 5/2014 | Chu et al. |
| 8,728,145 B2 | 5/2014 | Chuter et al. |
| 2002/0022853 A1 | 2/2002 | Swanson et al. |
| 2002/0042647 A1 | 4/2002 | Jang |
| 2002/0099392 A1 | 7/2002 | Mowry et al. |
| 2002/0099393 A1 | 7/2002 | Fleischman et al. |
| 2002/0123790 A1 | 9/2002 | White et al. |
| 2003/0070676 A1 | 4/2003 | Cooper et al. |
| 2003/0109893 A1 | 6/2003 | Vargas et al. |
| 2003/0125797 A1 * | 7/2003 | Chobotov ................ A61F 2/07 623/1.13 |
| 2003/0144578 A1 | 7/2003 | Koster, Jr. |
| 2003/0176878 A1 | 9/2003 | Bolduc et al. |
| 2003/0216749 A1 | 11/2003 | Ishikawa et al. |
| 2004/0093058 A1 * | 5/2004 | Cottone ................ A61F 2/07 623/1.11 |
| 2004/0097991 A1 | 5/2004 | Vargas et al. |
| 2004/0102794 A1 | 5/2004 | Roy et al. |
| 2004/0107004 A1 | 6/2004 | Levine et al. |
| 2004/0116946 A1 | 6/2004 | Goldsteen et al. |
| 2004/0133221 A1 | 7/2004 | Sancoff et al. |
| 2005/0038455 A1 * | 2/2005 | Bates ................ A61F 2/064 606/153 |
| 2005/0049675 A1 * | 3/2005 | Wallace ................ A61B 17/11 623/1.13 |
| 2005/0049678 A1 * | 3/2005 | Cocks ................ A61F 2/91 623/1.15 |
| 2005/0137677 A1 | 6/2005 | Rush |

(56) References Cited

U.S. PATENT DOCUMENTS

| | | |
|---|---|---|
| 2005/0154448 A1 | 7/2005 | Cully et al. |
| 2005/0171593 A1* | 8/2005 | Whirley .............. A61F 2/06 623/1.13 |
| 2005/0171598 A1 | 8/2005 | Schaffer |
| 2005/0192604 A1 | 9/2005 | Carson et al. |
| 2005/0228409 A1 | 10/2005 | Coppi |
| 2005/0267559 A1 | 12/2005 | De Oliveira |
| 2005/0283173 A1 | 12/2005 | Abbott |
| 2006/0142840 A1* | 6/2006 | Sherry .............. A61F 2/86 623/1.13 |
| 2007/0055358 A1 | 3/2007 | Krolik et al. |
| 2007/0073388 A1 | 3/2007 | Krolik et al. |
| 2007/0106313 A1 | 5/2007 | Golden et al. |
| 2007/0179590 A1 | 8/2007 | Lu et al. |
| 2007/0185567 A1 | 8/2007 | Heuser et al. |
| 2007/0203572 A1 | 8/2007 | Heuser et al. |
| 2007/0293940 A1 | 12/2007 | Schaeffer et al. |
| 2008/0082159 A1 | 4/2008 | Tseng et al. |
| 2008/0109069 A1* | 5/2008 | Coleman .............. A61B 17/11 623/1.25 |
| 2008/0154290 A1 | 6/2008 | Golden et al. |
| 2008/0288044 A1 | 11/2008 | Osbourne |
| 2009/0030502 A1 | 1/2009 | Sun et al. |
| 2009/0036817 A1 | 2/2009 | Dakin et al. |
| 2009/0076587 A1 | 3/2009 | Gully et al. |
| 2009/0112237 A1* | 4/2009 | Paul, Jr. .............. A61F 2/06 606/155 |
| 2009/0143793 A1 | 6/2009 | Chua et al. |
| 2009/0209855 A1 | 8/2009 | Drilling et al. |
| 2010/0010613 A1 | 1/2010 | Dorn |
| 2010/0022940 A1* | 1/2010 | Thompson .............. A61B 17/11 604/9 |
| 2010/0023110 A1* | 1/2010 | Schaeffer .............. A61F 2/07 623/1.13 |
| 2010/0036401 A1 | 2/2010 | Navia |
| 2010/0241218 A1 | 9/2010 | Bruszewski et al. |
| 2010/0280612 A1 | 11/2010 | Helmus |
| 2011/0031656 A1 | 2/2011 | Anneaux et al. |
| 2011/0118821 A1 | 5/2011 | Brocker et al. |
| 2011/0172684 A1 | 7/2011 | Granja Filho |
| 2011/0184329 A1 | 7/2011 | Kramer et al. |
| 2011/0184507 A1* | 7/2011 | Fischer, Jr. .............. A61F 2/91 623/1.16 |
| 2011/0245851 A1* | 10/2011 | Ducharme .............. A61B 17/0057 606/151 |
| 2011/0264196 A1 | 10/2011 | Savage et al. |
| 2011/0282368 A1 | 11/2011 | Swayze et al. |
| 2012/0035708 A1* | 2/2012 | Paul, Jr. .............. A61F 2/07 623/1.16 |
| 2012/0065652 A1 | 3/2012 | Cully |
| 2012/0123513 A1 | 5/2012 | Asfora et al. |
| 2012/0290065 A1 | 11/2012 | Li et al. |
| 2013/0035752 A1 | 2/2013 | Chang |
| 2013/0085565 A1 | 4/2013 | Eller et al. |
| 2013/0274646 A1 | 10/2013 | Paris et al. |
| 2014/0031785 A1 | 1/2014 | Swhwagten et al. |
| 2014/0088685 A1 | 3/2014 | Yevzlin et al. |
| 2014/0121585 A1 | 5/2014 | Baker et al. |
| 2014/0194910 A1 | 7/2014 | Orion et al. |
| 2017/0000939 A1 | 1/2017 | Cully et al. |
| 2017/0196676 A1 | 7/2017 | Donadio et al. |

FOREIGN PATENT DOCUMENTS

| | | |
|---|---|---|
| CA | 2766347 A1 | 12/2010 |
| CA | 2810671 A1 | 3/2012 |
| JP | 2006-523515 A | 10/2006 |
| WO | WO 98-02099 A1 | 1/1998 |
| WO | WO-98-19629 A2 | 5/1998 |
| WO | WO-98-19636 A2 | 5/1998 |
| WO | WO 1999-45861 A1 | 9/1999 |
| WO | WO 99-62415 A1 | 12/1999 |
| WO | WO 2001-12074 A1 | 2/2001 |
| WO | WO 2001-026562 A1 | 4/2001 |
| WO | WO 2001-49213 A2 | 7/2001 |
| WO | WO 2001-49213 A3 | 7/2001 |
| WO | WO-2004-010898 A1 | 2/2004 |
| WO | WO-2004-093966 A1 | 11/2004 |
| WO | WO 2006-028825 A1 | 3/2006 |
| WO | WO 2007-024964 A1 | 3/2007 |
| WO | WO 2008-157283 A1 | 12/2008 |
| WO | WO-2009-055651 A1 | 4/2009 |
| WO | WO 2010-121192 A1 | 10/2010 |
| WO | WO 2012-034108 A1 | 3/2012 |
| WO | WO 2012-117402 A1 | 9/2012 |

OTHER PUBLICATIONS

Japanese Office Action issued by the Japanese Patent Office (translated), regarding corresponding patent application Serial No. 2014-514937, dated Oct. 15, 2014; 6 pages.

Japanese Office Action issued by the Japanese Patent Office (translated), regarding corresponding patent application Serial No. 2014-516037, dated Oct. 15, 2014; 5 pages.

International Preliminary Report on Patentability issued by the International Bureau of WIPO, (Written Opinion dated Apr. 22, 2013), regarding corresponding application Serial No. PCT/US2012/067561; dated Dec. 24, 2014; 7 pages.

European Search Report issued by the European Patent Office,regarding correspondence patent application Serial No. 12799745.0; dated Feb. 12, 2015; 6 pages.

European Search Report issued by the European Patent Office, regarding correspondence patent application Serial No. 12800430.6; dated Feb. 17, 2015; 6 pages.

European Search Report issued by the European Patent Office regarding correspondence patent application Serial No. 12800335.7; dated Mar. 6, 2015; 6 pages.

JP 2006-510393 A / WO2004-016201 A2, Feb. 26, 2004, Cook Incorporated et al.

JP 2004-516914 A / WO 2002-058594 A1, Aug. 1, 2002, Solem.

Japanese Rejection Office Action, issued by the Japanese Patent Office regarding corresponding patent application Serial No. JP2015-517230; dated Nov. 16, 2015; 8 pages. (English translation).

Japanse Final Rejection Office Action, issued by the Japanese Patent Office regarding corresponding patent applicaiton Serial No. JP2014-516024; dated Jun. 4, 2016, 5 pages.

Japanese Final Rejection Office Action, issued by the Japanese Patent Office regarding corresponding patent application Serial No. JP2014-514937; dated Jun. 10, 2014; 7 pages.

Japanese Rejection Office Action, issued by the Japanese Patent Office regarding corresponding patent application Serial No. JP2014-516037; dated Jun. 4, 2014; 8 pages.

European Communication pursuant to Article 94(3) EPC, issued by the European Patent Office regarding corresponding patent application Serial No. EP 12799745.0, dated Dec. 20, 2016, 4 pages.

European Communication pursuant to Article 94(3) EPC, issued by the European Patent Office, regarding corresponding patent application Serial No. 12800430.6, dated Dec. 12, 2016, 4 pages.

International Search Report and Written Opinion issued by the ISA/U.S. Receiving Office, regarding corresponding application Serial No. PCT/US2012/067561; dated Apr. 22, 2013; 10 pages.

International Search Report and Written Opinion issued by the ISA/U.S. Receiving Office, regarding corresponding application Serial No. PCT/US2012/042639; dated Sep. 25, 2012; 9 pages.

International Search Report and Written Opinion issued by the ISA/U.S. Receiving Office, regarding corresponding application Serial No. PCT/US2012/042666; dated Sep. 13, 2012; 5 pages.

International Search Report and Written Opinion issued by the ISA/U.S. Receiving Office, regarding corresponding application Serial No. PCT/US2012/042688; dated Sep. 14, 2012; 9 pages.

"Anastomosis;" (n. d.) Dictionary.com Unabridged. Retrieved Jul. 30, 2017 from Dictionary.com website [http://www.dictionary.com/browse/anastomosis. 3 pages.

"Tine"; Merriam-Webster, n. d. Web. Aug. 22, 2018.

International Search Report and Written Opinion issued by the ISA/U.S. Receiving Office, regarding related application Serial No. PCT/US2019/017200; dated May 6, 2019; 13 pages.

(56) References Cited

OTHER PUBLICATIONS

International Search Report and Written Opinion issued by the ISA/U.S. Receiving Office, regarding related application Serial No. PCT/US2019/016970; dated May 8, 2019; 13 pages.

* cited by examiner

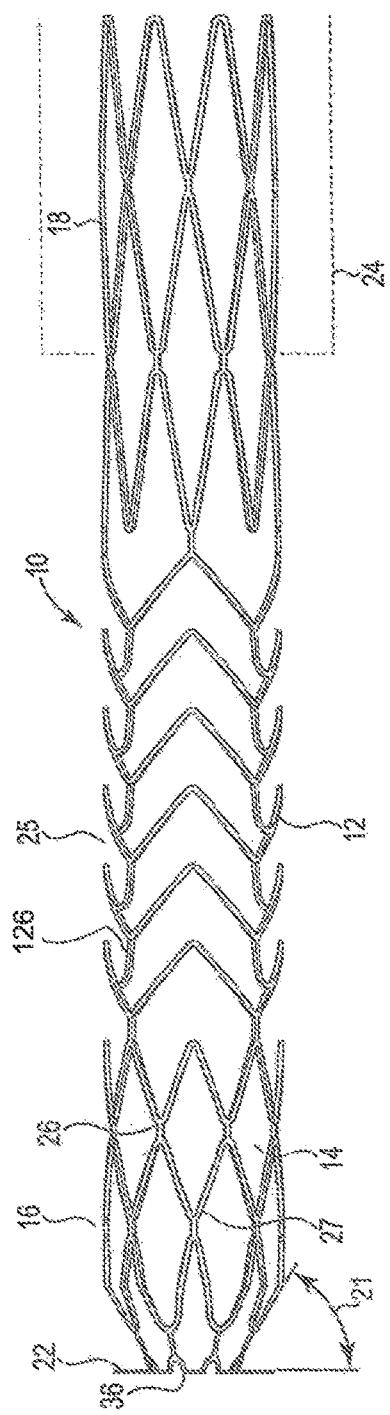
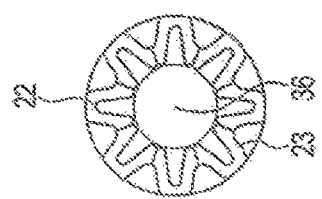

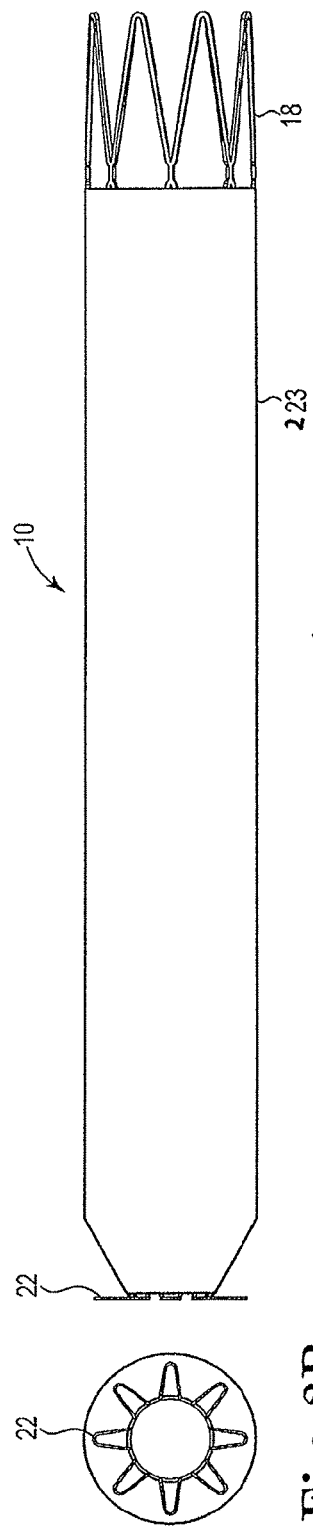
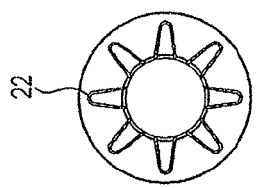
Fig. 2A
Fig. 2B

ARTERIAL AND VENOUS ANCHOR DEVICES FORMING AN ANASTOMOTIC CONNECTOR AND SYSTEM FOR DELIVERY

CROSS REFERENCE TO RELATED APPLICATIONS

This application is a U.S. national stage application of International application Serial No.: PCT/US2012/067561, filed on Dec. 3, 2012, which claims priority to International patent application Serial No.: PCT/US2012/042639, filed on Jun. 15, 2012; International patent application Serial No.: PCT/US2012/042666, filed on Jun. 15, 2012; International patent application Serial No.: PCT/US2012/042688, filed on Jun. 15, 2012; and U.S. Provisional application Ser. No. 61/683,898, filed on Aug. 16, 2012, the entireties of which are hereby incorporated by reference.

BACKGROUND OF THE INVENTION

Field of the Invention

This invention relates to medical devices for use in surgical procedures. More specifically, the present invention is related to medical devices that can be used for blood vessel anastomosis procedures.

Background of the Related Art

In the United States alone, approximately 400,000 people have end-stage renal disease requiring chronic hemodialysis. Hemodialysis replaces kidney function by removing toxins from the blood that are normally removed by healthy kidneys. In order to effectively remove toxins, blood must be passed at a high blood flow rate through a hemodialysis machine. This high blood flow is best achieved by the creation of a permanent vascular access site that includes an arteriovenous (AV) anastomosis in which a vein is attached to an artery to form a high-flow shunt or fistula.

Typically, a vein may be directly attached to an artery, but it can take up to twelve weeks before the fistula has sufficiently matured (time between placement and cannulation for dialysis) to provide adequate blood flow for use with hemodialysis. Moreover, a direct anastomosis may not be feasible in all patients due to anatomical considerations. Other patients may require the use of artificial graft material to provide an access site between the arterial and venous vascular systems. Because of the length of time required for a fistula to mature a patient needing dialysis will typically require a temporary access device, such as a Quinton catheter, to be inserted for hemodialysis access until the fistula has matured. The use of a temporary catheter access exposes the patient to additional risk of bleeding and infection, as well as discomfort, and is associated with a 91% higher mortality rate compared to fistulas. In trying to increase the prevalence of fistulas in the U.S., a proportional rise in catheter use has been documented.

Another method of using an anastomotic connector is in a coronary bypass procedure to form an end-to-side anastomosis of a saphenous vein to a coronary artery.

What is needed is an improved anastomosis device that addresses the foregoing problems.

BRIEF SUMMARY OF THE INVENTION

The present invention solves the foregoing problems and can find one non-limiting use in performing cardiac artery bypass grafts. In another non-limiting use the present invention can be used for procedures in which short-term and long-term vascular access is required. Another non-limiting use of the present invention is to provide an improved anastomotic connector for performing bypass operations.

In one non-limiting use, the present invention provides a percutaneous connection to be created between an artery and vein of a kidney failure patient without the need for surgery; which allows immediate cannulation of the shunt without reliance on catheter use; and which allows for the maturation of the outflow veins for subsequent conversion to a fistula.

In one aspect of the invention, an arterial anchor device is provided. Arterial anchor device includes a generally tubular main body having a distal end and a proximal end and defining a lumen therewithin. Generally tubular main body comprises a metal frame structure including struts and connector portions. The distal end, which is received within a vessel wall, includes a plurality of petal-like flanges circumferentially disposed about the distal end and integrally formed with tubular main body. The flanges may be configured to bend at an angle equal to or less than 90 degrees towards the longitudinal axis of the tubular main body portion or bend at an angle greater than 90 degrees away from the longitudinal axis of tubular main body portion. The flanges are configured to spread from a first reduced configuration to a second expanded configuration to anchor the arterial anchor device against the inner wall of an arterial fluid passageway. The distal end of the tubular main body portion is semi-rigid and configured to bend at an angle of approximately 90 degrees from the longitudinal axis of the tubular main body and maintain the bend. The struts and connectors that form the distal end, therefore, include a variable cutting pattern such that the frame-like structure of struts and connectors at the distal end are closer together than the struts and connectors that form the main body. The proximal end of tubular main body may optionally include a plurality of finger-like tines integrally formed with tubular main body. Finger-like tines extend outwardly at an acute angle from the longitudinal axis of the main body lumen. Finger-like tines are configured to securedly fasten a graft member in place when operably coupled with the tubular main body.

In another aspect of the present invention, a venous anchor device is provided. The venous anchor device includes a generally tubular main body having a distal end and a proximal end and defines a lumen therewithin. Generally tubular main body comprises a metal frame structure. The distal end, which is received within a vessel wall, includes first and second portions. In one embodiment the first and second portions are non-coated. Alternatively, the first portion may be coated and the second portion may be non-coated or exposed. The outer diameter of the distal end is larger than the outer diameter of the tubular main body portion. A plurality of barbs are circumferentially disposed about the second end and integrally formed with tubular main body. The plurality of barbs are configured to seat the venous anchor device in the vessel wall to ensure it does not dislodge from the vessel and also to prevent the further expansion of the vein when the barbs contact the vessel wall. A portion of the tubular main body is coated with PTFE in the manner described herein to prevent leaking. The second portion of the distal end of the venous anchor device is non-coated to ensure that barbs are free to secure the venous anchor device to the venous wall.

In another aspect of the invention, an anastomotic connector is provided that includes an arterial anchor device, a venous anchor device; and a graft member. The arterial anchor device and venous anchor devices are as described hereinbefore. A graft portion comprising a generally tubular main body having a reinforced wall is structured to join the arterial and venous anchor devices within a patient's body. The tubular body including first and second ends thereof and defines a lumen therewithin. The outer diameter of the stented tubular main body of the arterial anchor device is greater than the inner diameter of the graft lumen thus providing an interference fit when in operable engagement. Optional finger-like tines on the proximal end of the arterial anchor device may also exert force against graft portion and prevent graft portion from being easily removed from the arterial connector. The second end of graft member is similarly connected to the venous anchor device, which is received within the lumen of the venous anchor device, which is configured to be placed within a second fluid passageway. The OD of the venous anchor device is greater than the ID of the graft resulting in a compression or friction fit when operably coupled. In position the arterial and venous anchor devices fluidly couple a first fluid passageway to a second fluid passageway to form an anastomotic connector.

In another aspect of the present invention, the arterial and venous anchor devices are coated with a PTFE coating to prevent leakage of blood or other fluids from the portion of the device that transports fluid from the first anchor device through the graft and to the second anchor device. The PTFE coating is applied by a process including forming a dispersion of polymeric nanofibers, a fiberizing polymer, and a solvent, the dispersion having a viscosity of at least about 50,000 cPs. The arterial and venous anchor devices are positioned over a tubular polymeric structure. Nanofibers from the dispersion are electrospun onto the tubular frame of the device and then the devices are heated. The process for coating the arterial and venous anchor devices is disclosed in U.S. 20110031656 and 20010030885 which are hereby incorporated by reference in their entirety. Alternatively, the arterial and venous anchor devices are coated by extruding tubes of polytetrafluoroethylene (PTFE) on the inside of the device and one on the outside. The two layers that are formed are heated to meld together. Other polymers that may be useful in coating the present devices are fluorinatedethylenepropylene (FEP), perfluoroalkoxy (PFA), polyvinylidene fluoride (PVDF), tetrafluoroethylene, hexafluoropropylene, polyethylenes such as HDPE, MDPE and LDPE, polyethylene terepthalate polyester (PET), polyetheretherketone (PEEK) and similar polymers having low coefficients of friction.

In another aspect of the invention, an anastomotic connector is provided that includes an arterial anchor device, a venous anchor device; and a graft member as hereinbefore described.

In another aspect of the present invention, a method of delivering an arterial anchor device within an arterial fluid passageway is provided. The method includes providing an arterial anchor device, the arterial anchor device including a generally tubular main body having a distal end and a proximal end, said distal end integrally defining a plurality of petal-like flanges circumferentially disposed about the distal end of said tubular main body, said tubular main body and said flanges movable between a loaded configuration and a preset expanded configuration; optionally providing a seating device comprising a wire shaft and a balloon member adapted to be inflated and deflated, said wire shaft positioned within a lumen of said tubular main body and said balloon member extending past said flanges; providing a delivery device, said delivery device including an outer sheath having a lumen; compressibly loading said seating device and said arterial anchor device within the lumen of said outer sheath; deploying the delivery device through an access site into a fluid passageway of a vessel; retracting the outer sheath to expose said flanges, wherein upon retracting the outer sheath said flanges revert to the preset expanded configuration; optionally inflating said balloon member and causing said flanges to engage an inner surface of the fluid passageway by moving said wire shaft proximally to cause said balloon member to adjacently abut said flanges thereby seating the arterial anchor device in the fluid passageway; removing said delivery device and seating device from said vessel. The tubular main body may exit the delivery device in a straight configuration and subsequently be bent into place at an angle of approximately 90 degrees by the surgeon. Alternatively, the tubular main body may be preset to bend at an approximate 90 degree angle such that when it exits the delivery device it reverts to the pre-set configuration.

In another aspect of the present invention, a method of delivering a venous anchor device within a venous fluid passageway is provided. The method includes providing a venous anchor device, the venous anchor device having a generally tubular main body having a distal end and a proximal end, said distal end integrally defining a plurality of barbs configured to engage a vessel wall, said tubular main body and said barbs movable between a loaded configuration and a preset expanded configuration; providing a delivery device, said delivery device including an outer sheath having a lumen; compressibly loading said venous anchor device within the lumen of said outer sheath; deploying the delivery device through an access site into a venous fluid passageway of a vessel; retracting the outer sheath to expose the distal end of the venous anchor device, wherein upon retracting the outer sheath the barbs revert to the pre-set expanded position and seat the device against the venous vessel wall; removing said delivery device.

In another aspect of the invention, a method of forming an anastomotic connector between two vessels in a body of a patient is provided. The method providing an arterial anchor device, said arterial anchor device including an arterial anchor tubular main body having a distal end and a proximal end, said distal end integrally defining a plurality of flanges circumferentially disposed about the distal end of said tubular main body, said arterial anchor tubular main body and said plurality of flanges movable between a loaded configuration and preset expanded configuration; providing a delivery device, said delivery device including an outer sheath defining a lumen therewithin; compressibly loading said arterial anchor device within the lumen of said outer sheath; deploying the delivery device through an access site into a first fluid passageway of a vessel to a predetermined position; retracting the sheath to expose said flanges and said balloon member, wherein upon retracting the sheath said flanges revert to the preset expanded configuration, wherein said flanges engage the surface of a wall of said first fluid passageway; further retracting said outer sheath to cause said tubular main body to revert to the preset expanded configuration outside the vessel wall; bending said tubular main body at an angle of ninety degrees from the longitudinal axis of the device; withdrawing said delivery device from said vessel; operably connecting a first end of a length of graft material to the proximal end of said arterial anchor tubular main body; providing a venous anchor device, said venous anchor device including a venous anchor tubular main body having a distal end and a proximal end, said distal end integrally defining a plurality of barbs thereon, said tubular main body and said plurality of barbs movable between a loaded configuration and preset expanded configuration; compressibly loading said venous anchor device within the lumen of said outer sheath of said delivery device; deploying the delivery device through an access site into a second fluid passageway of a vessel to a predetermined position; retracting the sheath to expose the distal end of said venous vessel anchor and said barbs, wherein upon retracting the sheath said barbs and said distal end revert to the preset expanded configuration; further retracting said outer sheath to cause said venous anchor tubular main body to revert to the preset expanded configuration outside the vessel wall; withdrawing said delivery device from said second vessel; and forming said anastomotic connector by operably connecting a second end of said length of graft material to the proximal end of said venous tubular main body.

These and other features of the invention will now be described in detail with reference to the accompanying Figures.

BRIEF DESCRIPTION OF THE DRAWINGS

FIG. 1A is a side view of one exemplary embodiment of an arterial anchor device in accordance with the invention.

FIG. 1B is a detailed view of the distal end of the arterial anchor device showing petal-like flanges.

FIG. 2A is a perspective view of the arterial anchor device of FIG. 1 showing the device coated in accordance with the invention.

FIG. 2B is a detailed view of the distal end of the arterial anchor device showing uncoated petal-like flanges.

DETAILED DESCRIPTION OF THE INVENTION

Figure 1C:
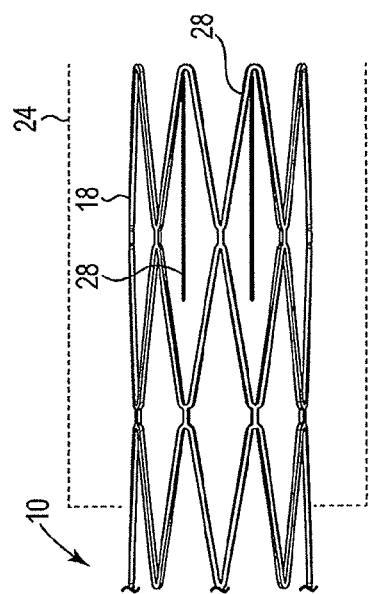
FIG. 1C is a side view of the proximal end of the arterial anchor device in accordance with the invention showing optional outwardly extending tines.

The invention is generally directed to an anastomotic connector structured to attach a graft between an artery and a vein, a novel arterial anchor device for anchoring the anastomotic connector to the artery and a novel venous anchor device for anchoring the anastomotic connector to the vein. The anastomotic connector in accordance with the invention may be placed percutaneously or subcutaneously and may be fabricated from any biocompatible material suitable for implantation into the human body. Further, the anchor devices preferably have a low cost and are readily replaceable. As will be appreciated by those of ordinary skill in the art based upon the following disclosure, the anastomotic connector of the invention may replace the use of catheters in those patients on hemodialysis who are permanently consigned to catheter use due to their inability (anatomically or otherwise) to sustain long-term fistula or graft options.

Numerous structural variations of an anastomotic connector device and arterial anchor devices are contemplated and within the intended scope of the invention. For purposes of discussion and not limitation, an exemplary embodiment will be described in detail below. As those of ordinary skill in the art will appreciate, although the anastomotic connector will be described with reference to placement within a vessel, it should be understood that the anastomotic connectors may be placed within various other fluid passageways without departing from the intended scope of the invention.

As best seen in FIGS. 1 through 6 the anastomotic connector system in accordance with the invention broadly comprises an arterial anchor device, a graft and a venous anchor device. The component parts of the anastomotic connector system will now be described.

FIG. 1A is a side view of one exemplary embodiment of an arterial anchor device 10 used to form the anastomotic connector in accordance with the invention. As illustrated in FIG. 1A, arterial anchor device 10 generally includes a tubular main body 12 defining a lumen 14 therethrough. Main body 12 includes distal 16 and proximal ends 18. In an exemplary embodiment, the outer diameter of proximal end 18 of main body 12 is greater than an outer diameter at the distal end 16 thereof. In other embodiments the outer diameter of the distal 16 and proximal 18 ends are substantially equivalent. The outer diameter of proximal end 18 may also be greater than the internal diameter of graft material 24 such that when the graft material 24 is received over the proximal end 18 of the main body 12, the radial force exerted by the anchor device at body temperature ensures an interference fit when operably coupled to graft material 24. One exemplary but non-limiting type of graft that may be used is a Vectra® vascular access graft (Bard Peripheral Vascular, Tempe, Ariz.). In other embodiments the outer diameter of proximal end 18 of main body 12 may be substantially equivalent to the internal diameter of the graft material so long as an interference fit is achieved, without departing from the intended scope of the invention. The varying outer diameters of the proximal end 18 of the main body 12 may depend upon numerous factors such as, for example, the desired amount of flow through the anastomotic connector. In exemplary embodiments the outer diameters of the proximal end 18 may range between about 1 mm and about 10 mm, although larger or smaller outer diameters are also contemplated and within the intended scope of the invention.

As illustrated in FIGS. 1A and 1B, arterial anchor device 10 includes a plurality of flanges 22 circumferentially disposed about the distal end 16 thereof. Flanges 22 have a petal-like configuration and are integrally formed with the tubular main body 12 of arterial anchor device 10. In forming the petal-like configuration flanges comprise a wire that in a second expanded configuration has a diameter across a central portion that is wider than the diameter across the first and second end portions. Flanges 22 may be configured to expand upon deployment at a preset angle equal to approximately 90 degrees or less. In one aspect of the invention, flanges 22 are offset at an acute angle 21 from the longitudinal axis of tubular main body 12 to seat the arterial anchor device against a vessel wall. In an exemplary embodiment, the acute angle may be approximately 50 to 60 degrees and may be preset at 55 degrees. In one aspect of the invention in a first non-expanded configuration flanges 22 are substantially parallel to a longitudinal axis of the tubular body. In another aspect of the invention, in a second expanded configuration, flanges 22 are substantially perpendicular to the longitudinal axis of the tubular body. In another aspect of the invention in a second expanded configuration, flanges 22 are offset from the longitudinal axis of the tubular main body by an acute angle.

As best seen in FIG. 1B, the struts or wires 23 that form the wall of the petals are configured to expand into a wider profile to ensure that they contact the maximum area possible of the vessel wall thus ensuring the proper seating of the arterial anchor device against the wall of the arterial fluid passageway. Those of skill in the art will also appreciate that various configurations could be made to flanges 22, without departing from the intended scope of the invention, so long as the flanges 22 are sufficiently angled and sufficiently spread apart to securely and firmly anchor the arterial anchor device 10 to a vessel wall in an arterial fluid passageway. Those of skill in the art will appreciate, however, that the petals which are formed axially will be flatter against the vessel wall and, therefore, provide greater anchoring than the petals that are otherwise formed.

For purposes of this disclosure, however, flanges 22 configured at an acute angle 21 offset from the longitudinal axis of main body 12 will be discussed. Tubular main body 12 comprises a metal frame structure that includes integrally formed struts 27 and connectors 26. Referring to FIG. 1C, arterial anchor device 10 may optionally include a plurality of finger-like tines 28 positioned at the proximal end 18 of tubular main body 12 and integrally formed therewith. Finger-like tines 28 extend outwardly from the main body 12 at an acute angle. However, those of skill in the art will appreciate that finger-like tines 28 can extend outwardly from the main body lumen 14 at any angle that will cause them to exert a compressive force on a graft when operably coupled therewith. Tubular graft portion 24 is operably coupled to proximal end 18 of main body 12 by inserting the proximal end 18 of arterial anchor device 10 into the lumen of the graft 24. Because finger-like tines 28 extend outwardly from the tubular main body lumen 14 they exert a compressive force on graft 20 that prevents the graft 20 from being retracted in the opposite or proximal direction thus operably coupling the tubular graft portion 24 to arterial anchor device 10 assuring the graft will not dislodge after placement.

Figure 1D:
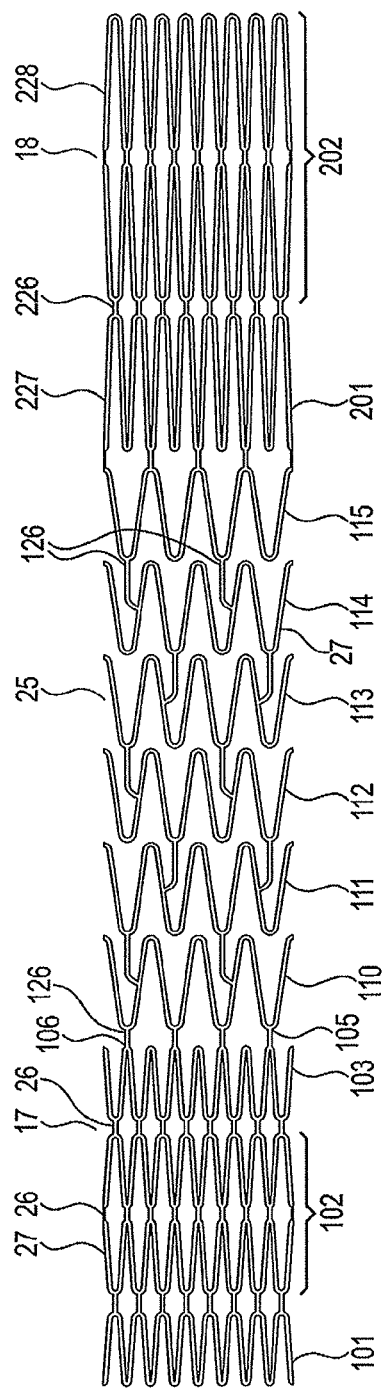
FIG. 1D is a detailed view of the frame work structure of the arterial anchor device laid flat in accordance with an aspect of the invention.

As further illustrated in the exemplary embodiment of FIGS. 1A-1D, tubular main body 12 integrally transitions at the distal and proximal ends into flanges 22 and finger-like tines 28, respectively. Tubular main body 12 includes a distal end 16 and a proximal end. As can best be seen in FIG. 1D the struts 27 that form the distal end 16 have a variable cutting pattern 17 resulting in struts 27 that are closer together and more tightly formed than the struts 27 that form the central portion 25 and those at the proximal end 18. As can be seen in FIG. 1D, the strut formation at the distal end 16 includes three sections 101, 102, 103. The first and thirds sections 101, 103 include a plurality of sinusoidal-shaped struts having a length of approximately 3.77 mm. The second section 102 includes double sinusoidal-shaped struts connected at the curve by connecting member 26. The second section 102 is connected to the first and third sections 101, 103 by additional connecting members 26. The second section is approximately 8.8 mm.

The central portion 25 also includes a plurality of rows 110-115 of openly-formed sinusoidal-shaped struts. The first row of struts 110 is connected at the curved portion 105 of the strut to the curved portion 106 of the last row of struts in the distal end. Each row of central portion struts 110-115 is connected to the subsequent row by two connecting members 126 that extend from a mid-portion of the strut to the curved portion of the strut in the subsequent row. Central portion 25 is approximately 28 mm.

The elongated proximal end includes a strut formation of two rows 201, 202. Each row includes a plurality of sinusoidal-shaped struts 227 with the second section 202 including double sinusoidal-shaped struts 228. First row 201 is connected by a plurality of connecting members 226 to the central portion 25. First row 201 connected at the curved portion to the second double row 228.

Those of skill in the art will appreciate that the number of rows utilized in the anchor device can vary depending on the length of the anchor device desired.

The arterial anchor device in accordance with the invention is expandable from a first retained configuration to a second expanded configuration as seen in FIG. 1A. The variable cutting pattern of the distal end 16 allows for the second configuration in which the distal end 16 may be bent or preset at an angle that is approximately 90 degrees offset from the longitudinal axis LA of the tubular main body 12 as best seen in FIG. 3B. In addition, the tighter variable cutting pattern of the distal end provides a stronger radial force when in the expanded position which helps in preventing leakage when positioned within an arterial vessel. The stronger radial force at the distal end also prevents the arterial anchor device from collapsing and cutting off or reducing flow through the anastomotic connector.

Plurality of flanges 22 are structured to move between a loaded position (inside a delivery sheath, not shown) prior to deployment and an expanded in situ position as illustrated in FIG. 1A and FIG. 3. As will be appreciated by those of ordinary skill in the art, the arterial anchor device 10 in accordance with the invention, and as best seen in FIGS. 2A, 2B and 3, is structured to provide a secure, leak-free connection to an arterial vessel passageway. Therefore, it is contemplated that a fluid impermeable, biocompatible polymer 223 may be deposited on the arterial anchor device to fill the interstices of the struts comprising the tubular main body to ensure a leak-tight seal when implanted in the arterial fluid passageway. Such biocompatible materials may include, but are not limited to, expanded Polytetrafluoroethylene ("ePTFE"), polyester, silicone composites, or various other plastics and elastomers or combinations thereof. In an exemplary embodiment, the arterial anchor device is coated with a PTFE coating to prevent leakage of blood or other fluids from the portion of the device that transports fluid from the first anchor device through the graft and to the second anchor device. The PTFE coating is applied by a process including forming a dispersion of polymeric nanofibers, a fiberizing polymer, and a solvent, the dispersion having a viscosity of at least about 50,000 cPs. The arterial anchor device is positioned over a tubular polymeric structure. Nanofibers from the dispersion are electrospun onto the tubular frame of the device and then the devices are heated.

FIG. 3 depicts a further aspect of an anchor device in accordance with the invention having petal-like flanges 22 coated with the PTFE electrospun coating, those of skill in the art will appreciate that flanges 22 may remain uncoated as shown in FIGS. 2A and 2B to ensure a tight compression fit against the wall of the arterial fluid passageway. In addition, endothelialization of the flanges will be promoted by leaving flanges 22 uncoated. Further, it may to desirable to leave proximal end 18 uncoated so that the coating does not fray when it is compress into graft material 24 thus ensuring a fluid impermeable fit.

Alternatively, the arterial and venous anchor devices may be coated by extruding tubes of polytetrafluoroethylene (PTFE) on the inside of the device and one on the outside. The two layers that are formed are heated to meld together. Other polymers that may be useful in coating the present devices are fluorinatedethylenepropylene (FEP), perfluoroalkoxy (PFA), polyvinylidene fluoride (PVDF), tetrafluoroethylene, hexafluoropropylene, polyethylenes such as HDPE, MDPE and LDPE, polyethylene terepthalate polyester (PET), polyetheretherketone (PEEK) and similar polymers having low coefficients of friction.

Arterial anchor device 10 may be either self-expanding, such as so-called shape-memory materials, or non self-expanding, such as stainless steel. One benefit of using a self-expanding material is that plurality of flanges 22 will expand when deployed within a vessel without the need for a separate expansion device, thus eliminating additional equipment and steps during the deployment process.

As best seen in FIG. 1D, in forming the exemplary arterial anchor device 10, a tubular length of metal is used to cut the arterial anchor device 10 and integrally form the struts 24 and connectors 26 of tubular main body 12 as well as flanges 22 and finger-like tines 28. As discussed previously, the metal material used in the exemplary arterial anchor device 10 should be both resilient and capable of being heat treated to substantially set a desired shape. Preferably, the metal from which arterial anchor device 10 is cut exhibits a high modulus of elasticity that is biocompatible and has superior compressibility allowing the arterial anchor device 10 to be self-expandable.

One class of materials which meet these qualifications is so-called shape memory alloys. Such alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration unless constrained from so doing.

One particularly preferred shape memory alloy for use in the present method is Nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here.

Such NiTi alloys are preferred, at least in part, because they are commercially available, have a high yield strain and more is known about handling such alloys than other known shape memory alloys. NiTi alloys are also very elastic—they are said to be "superelastic" or "pseudoelastic." This elasticity will help a device of the invention return to a present expanded configuration for deployment into a blood vessel. However, any suitable self-expanding material may be used as will be appreciated by those of ordinary skill in the art.

As hereinafter described, prior to implantation the arterial anchor device 10 is collapsed inside a delivery device or sheath. Upon introduction into a vessel, the distal end of the anchoring structure freely self-expands to its original dimensions. The self-expanding behavior of the arterial anchor device 10 is due to the relatively high modulus of elasticity of the shape-memory material, which imparts superior spring-like properties to the arterial anchor device 10.

Figure 3A:
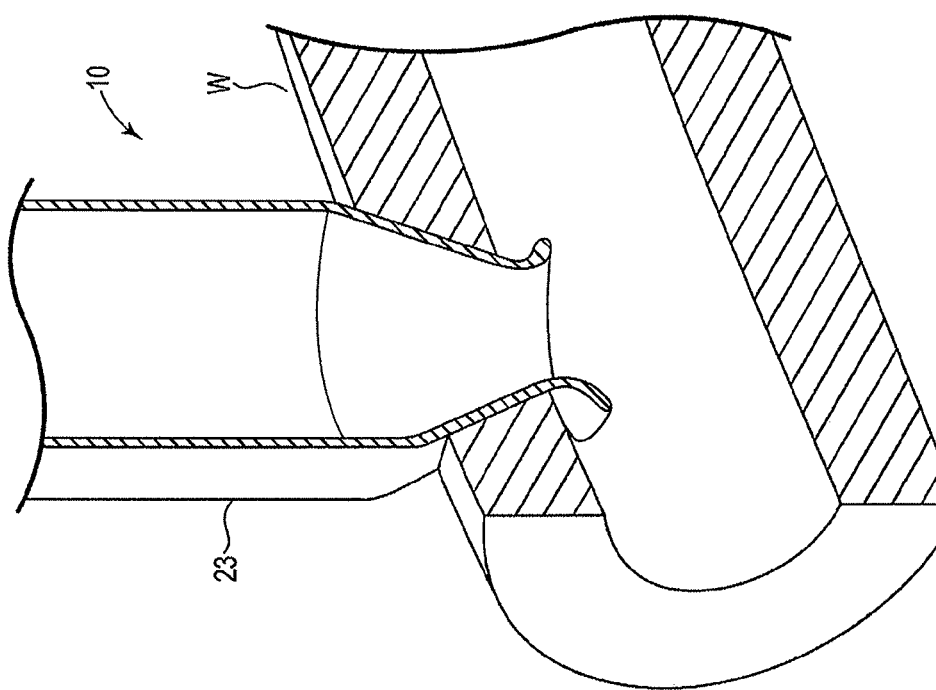
FIG. 3A is an illustration of a coated arterial anchor device positioned within an arterial fluid passageway.
Figure 3B:
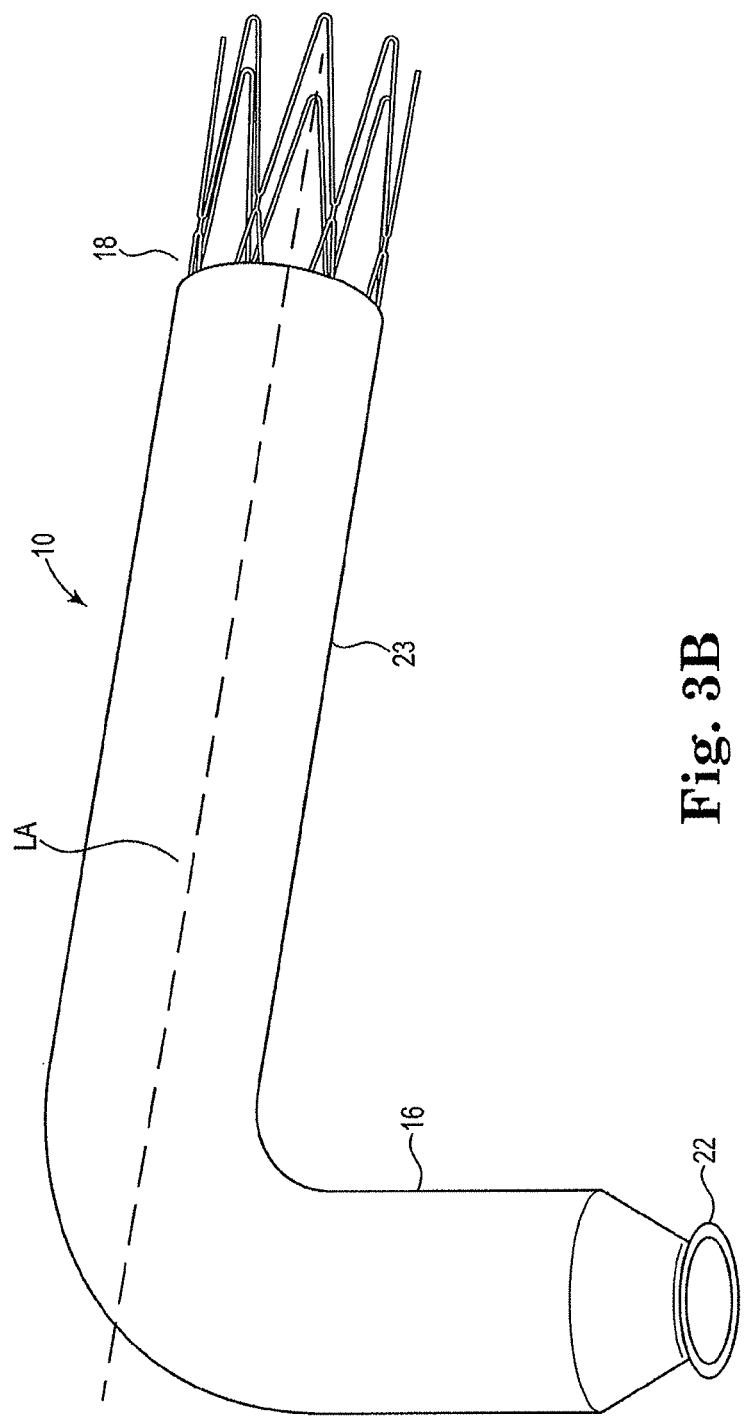
FIG. 3B is an illustration of the arterial anchor device with a bend between the distal end and the central portion of the tubular body which causes the distal end to be off-set from the longitudinal axis of the tubular body by about 90 degrees.

FIG. 3A illustrates an exemplary arterial anchor device 10 deployed through vessel wall W. FIG. 3B illustrates the approximate 90 degree bend in the arterial anchor device.

Figure 4A:
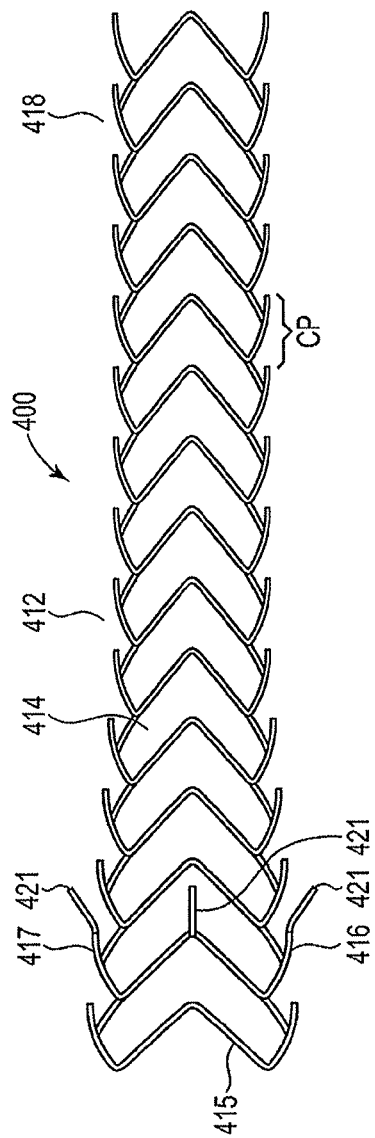
FIG. 4A is a side view of an embodiment of the venous anchor device in accordance with an aspect of the invention showing the frame work structure.
Figure 4B:
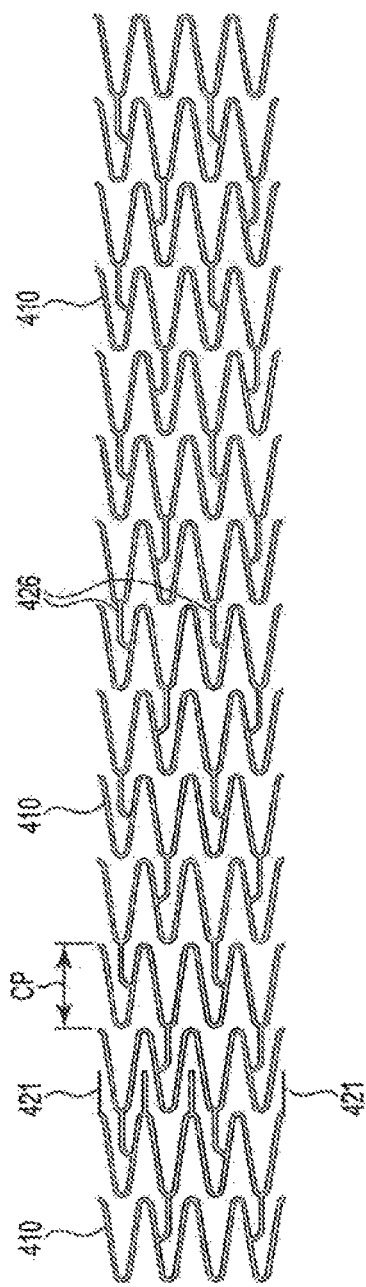
FIG. 4B is a view of the frame work structure of the venous anchor device laid flat in accordance with an aspect of the invention.
Figure 4C:
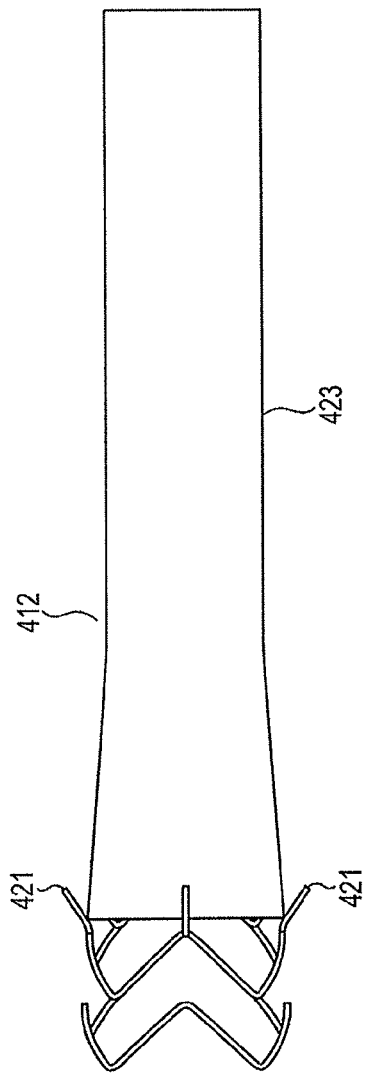
FIG. 4C is a side view of an aspect of the venous anchor device showing the device coated in accordance with the invention.
Figure 5:
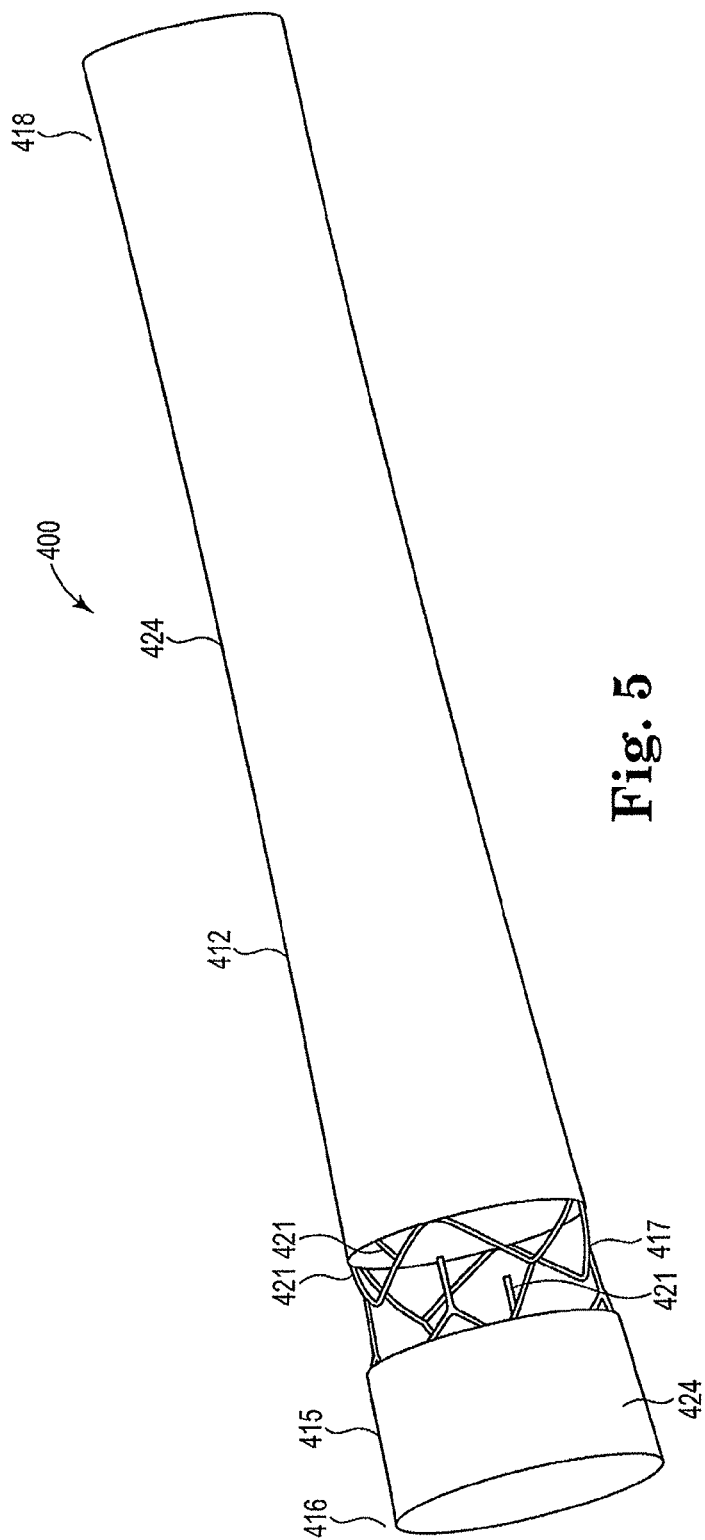
FIG. 5 is a perspective view of an alternative coated venous anchor device in accordance with the invention.
Figure 6:
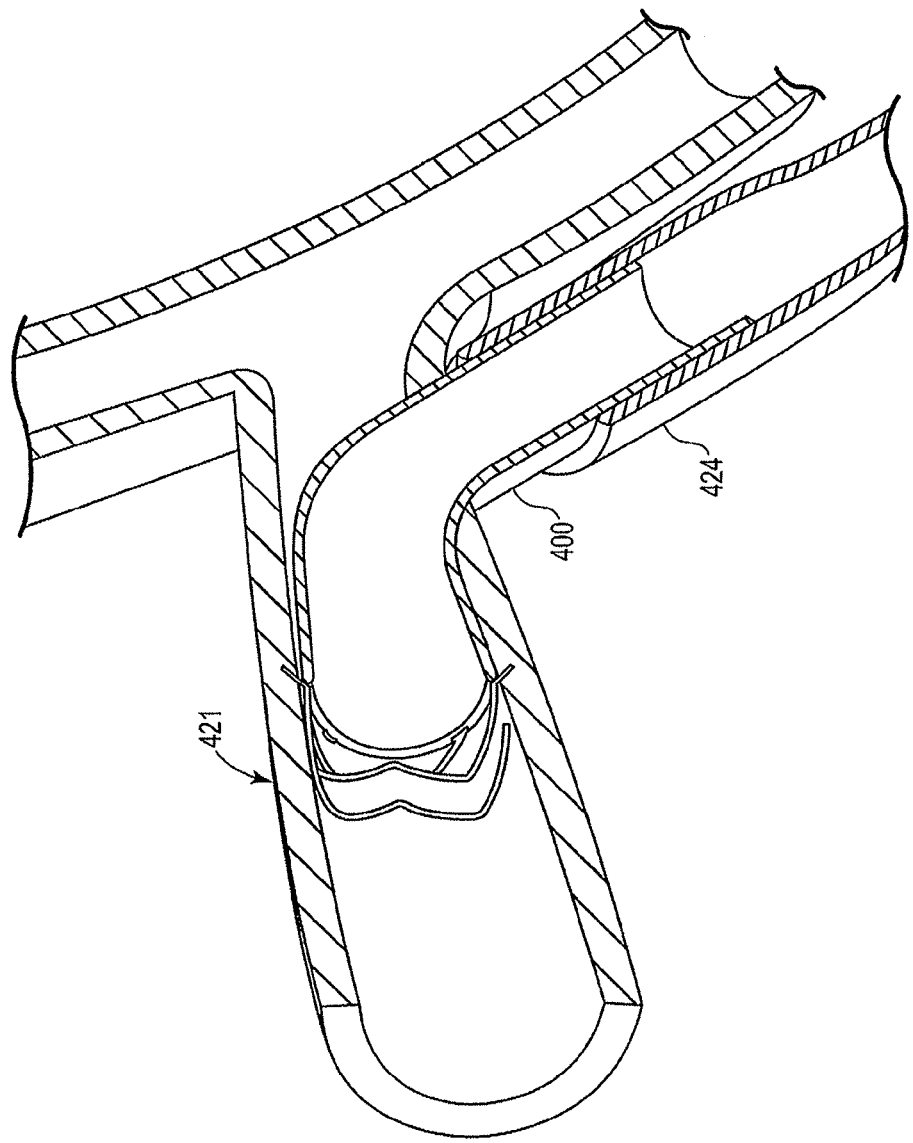
FIG. 6 is an illustration of the venous anchor device of FIG. 4 seated in a venous fluid passageway and connected to a graft portion.
Figure 7:
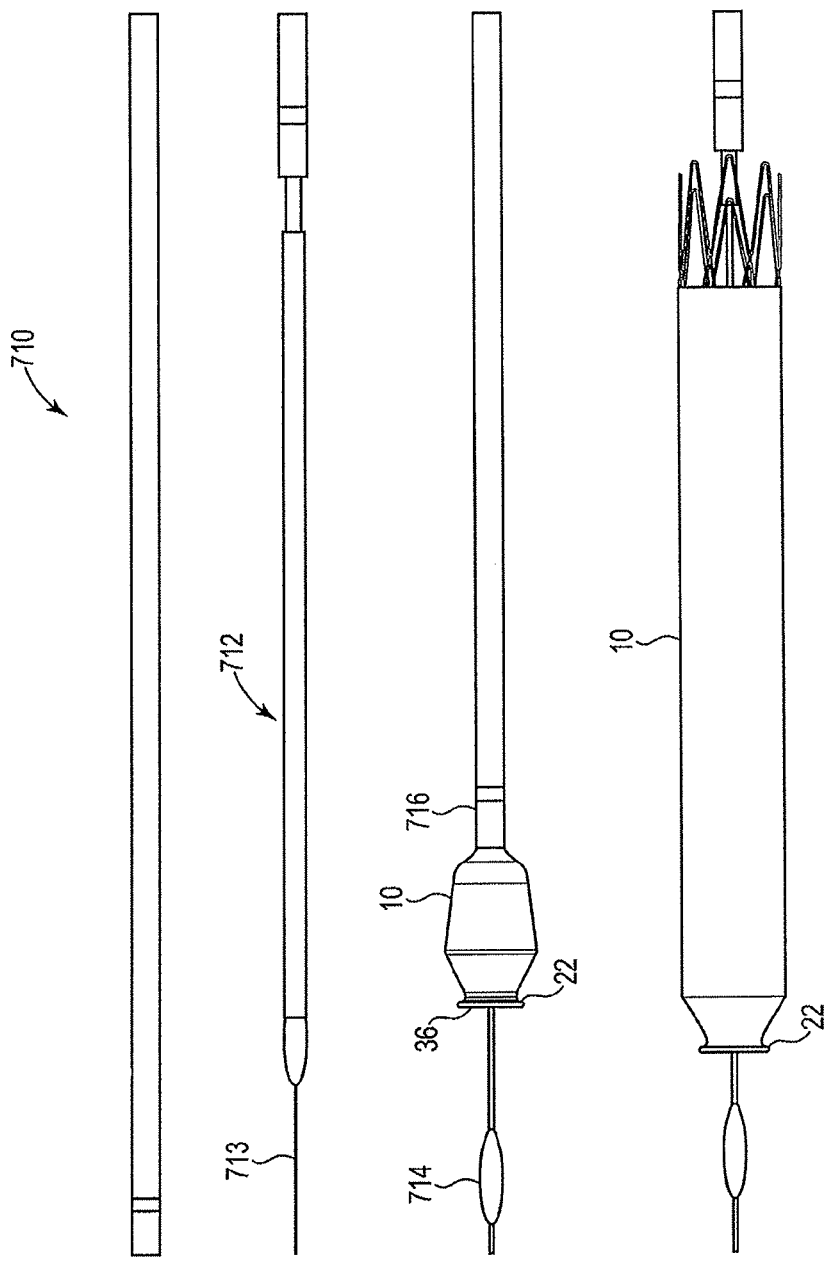
FIG. 7 illustrates an exemplary delivery device utilized to deliver the arterial and venous anchor devices in accordance with the invention.
Figure 8:
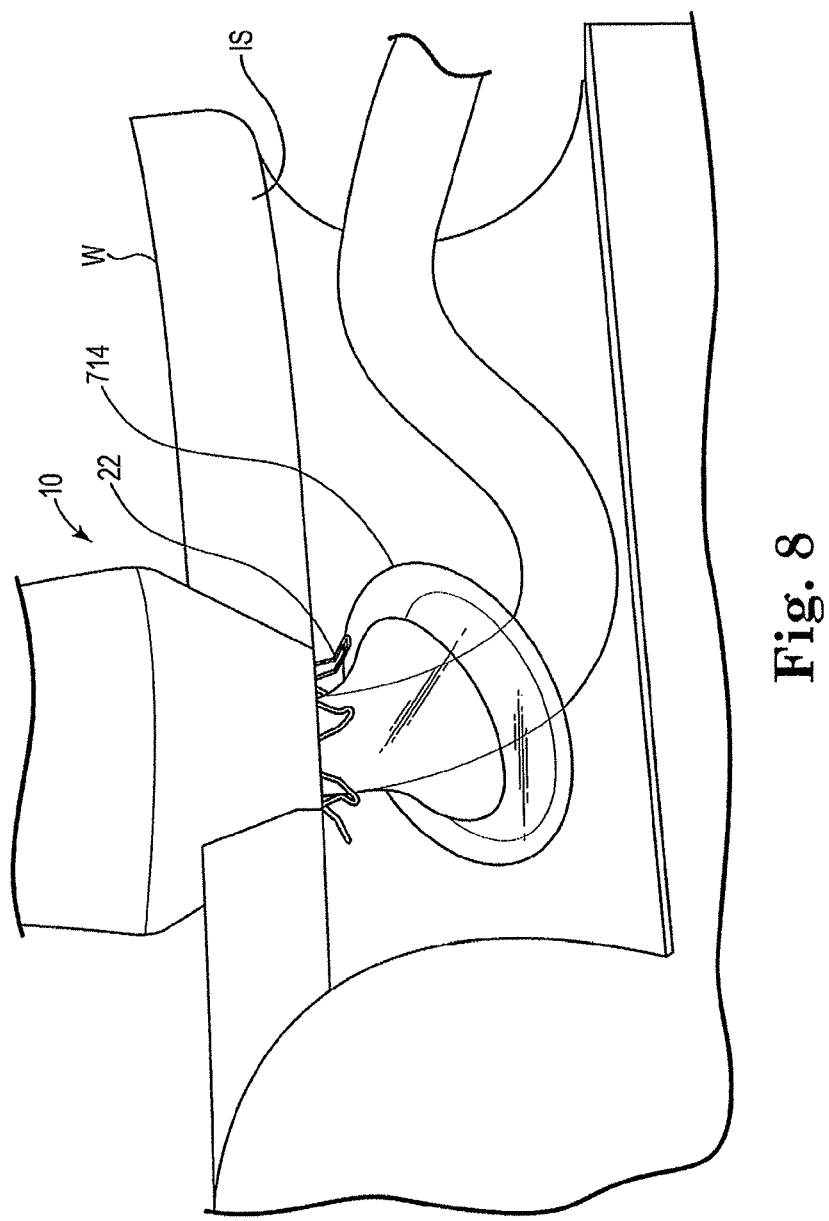
FIGS. 8-10 illustrate the delivery and method of placing the arterial anchor device within a vessel.
Figure 9:
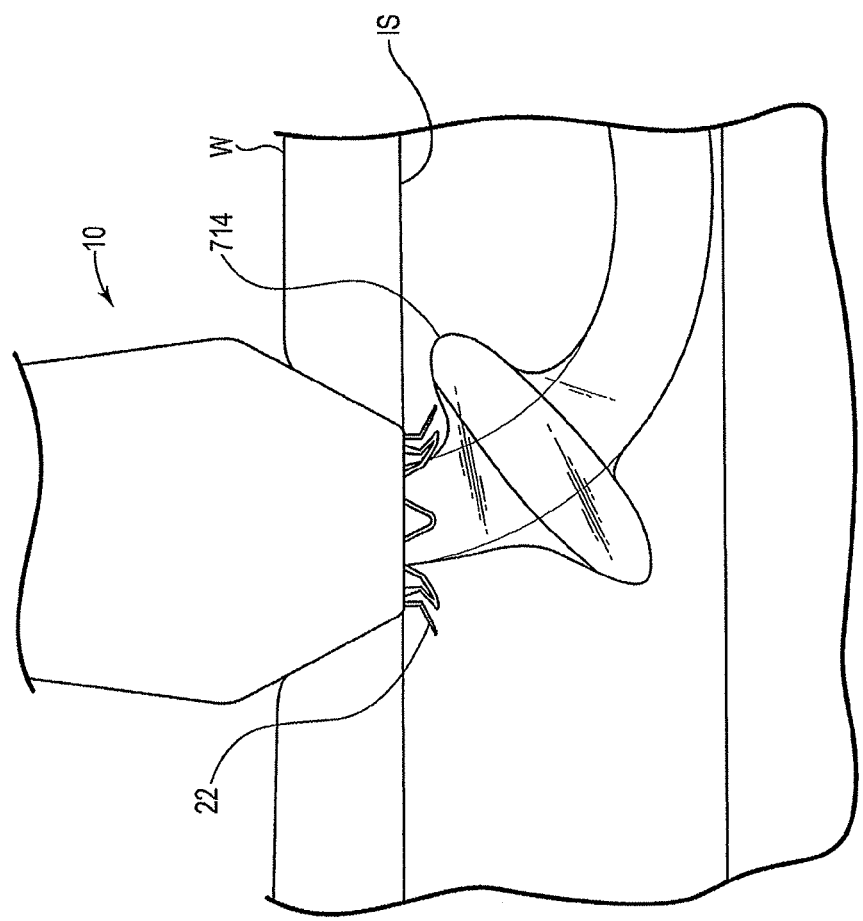
Figure 10:
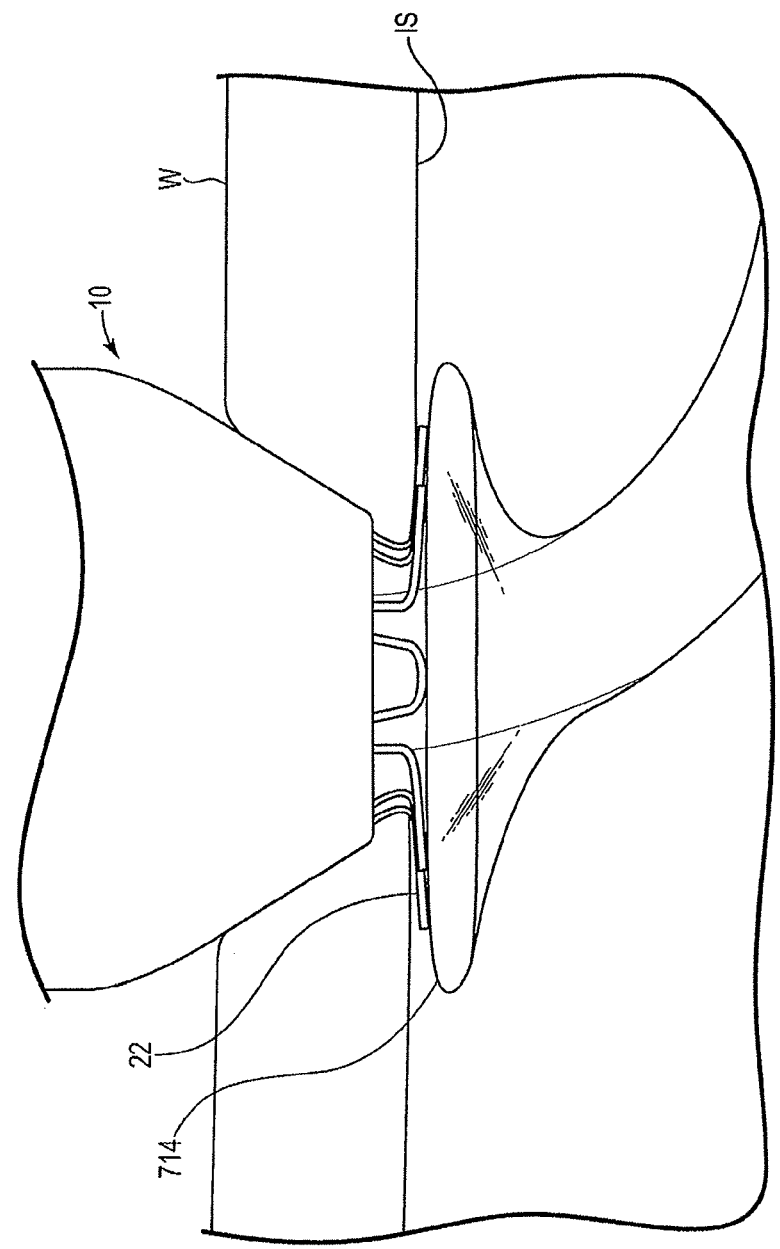

Referring now to FIGS. 4-6 a venous vessel anchor 400 in accordance with the invention is shown. As illustrated in FIG. 4A, venous vessel anchor 400 generally includes a tubular main body 412 defining a lumen 414 therethrough. Main body 412 includes distal 416 and proximal ends 418. In one exemplary embodiment, the outer diameter of distal end 416 of main body 12 is greater than the outer diameter of proximal end 418 to ensure it is property seated in a venous fluid passageway. Generally tubular main body 412 comprises a metal frame structure. In an exemplary embodiment depicted in FIG. 4C the distal end 416, which is received within a vessel wall, includes first and second portions 415, 417. The first 415 and second 417 portions are non-coated. Alternatively, as best seen in FIG. 5 the first portion 415 may be coated and the second portion may be non-coated to expose a plurality of barbs 421 circumferentially disposed about the second end and integrally formed with tubular main body. The plurality of barbs 421 are configured to seat the venous anchor device in the vessel wall to ensure it does not dislodge from the vessel wall. In addition, upon deployment barbs 421 restrict further expansion of the venous anchor device when the barbs 421 anchor it against the vessel wall. A portion of the tubular main body 412 is coated in the manner hereinafter described to prevent leaking. Preferably, the first and second portions 415, 417 of the distal end 416 of the venous anchor device are non-coated to ensure that barbs 421 are free to secure the venous anchor device 400 to the venous wall. When forming the anastomic connector in accordance with the invention, the venous vessel anchor 400 is operably coupled to graft material 424, as best seen in FIG. 6. One exemplary but non-limiting type of graft that may be used is a Vectra® vascular access graft (Bard Peripheral Vascular, Tempe, Ariz.). The outer diameter of proximal end 418 of main body 412 may be greater than the internal diameter of the graft material 424 to ensure a tight interference fit. Alternatively, the outer diameter of the proximal end 18 may be substantially equivalent to the internal diameter of the graft material, without departing from the intended scope of the invention, so long as an interference fit is achieved. The varying outer diameters of the proximal end 418 of the main body 412 may depend upon numerous factors such as, for example, the desired amount of flow through the anastomotic connector. In exemplary embodiments the outer diameters of the proximal end 418 may range between about 1 mm and about 10 mm and preferably about 8 mm on the proximal end when fully expanded, although larger or smaller outer diameters are also contemplated and within the intended scope of the invention. The outer diameter of the distal end 416 is approximately 10 mm to 12 mm and preferably 11 mm so long as it is larger than the proximal end 418.

As best seen in FIGS. 4A and 4B the frame-like structure of the tubular main body 412 has a loose configuration or in other words a column pitch that is substantially equivalent along the length of the device. in one aspect of the invention, the column pitch ("CP") is approximately 0.185 inches which allows the tubular body to easily bend. Those of skill in the art will appreciate, however, that other column pitches can be used and still be within the scope of the invention. When the tubular main body 412 is exposure to arterial pressure the loosely configured tubular main body 412 will stretch. When first deployed into the venous vessel it will assume an outer diameter equal to the inner diameter of the venous vessel into which it is deployed, up to an approximate maximum of about 10 mm, As barbs 421 engage the vessel wall (as best seen in FIG. 6) the barbs prevent the vein from further expansion.

As can be seen in FIG. 4B the frame like structure is substantially the same as the central portion 25 of the arterial anchor device 10. Thus, frame of the venous anchor device includes a plurality of rows 410 of openly-formed sinusoidal-shaped struts. Each row of struts 410 is connected to the subsequent row by two connecting members 426 that extend from a mid-portion of the strut to the curved portion of the strut in the subsequent row.

As will be appreciated by those of ordinary skill in the art, the venous anchor device 400 in accordance with the invention, and as best seen in FIGS. 4 through 6, is structured to provide a secure, leak-free connection to a venous vessel passageway. Therefore, it is contemplated that a fluid impermeable, biocompatible polymer 423 may be deposited on the venous anchor device 400 to the interstices of the struts comprising the tubular main body to ensure a leak-tight seal when implanted in the venous fluid passageway. The fluid impermeable, biocompatible polymer 423 may be woven. Such biocompatible materials may include, but are not limited to, expanded Polytetrafluoroethylene ("ePTFE"), polyester, silicone composites or various other plastics and elastomers or combinations thereof. In an exemplary embodiment, the venous anchor device is coated with a PTFE coating to prevent leakage of blood or other fluids from the portion of the device that transports fluid from the first anchor device through the graft and to the second anchor device. The PTFE coating is applied by a process including forming a dispersion of polymeric nanofibers, a fiberizing polymer, and a solvent, the dispersion having a viscosity of at least about 50,000 cPs. The venous anchor device 400 is positioned over a tubular polymeric structure. Nanofibers from the dispersion are electrospun onto the tubular frame of the device and then the devices are heated. Alternatively, the venous anchor device is coated by extruding tubes of polytetrafluoroethylene (PTFE) on the inside of the device and one on the outside. The two layers that are formed are heated to meld together. Other polymers that may be useful in coating the present devices are fluorinatedethylenepropylene (FEP), perfluoroalkoxy (PFA), polyvinylidene fluoride (PVDF), tetrafluoroethylene, hexalluoropropylene, polyethylenes such as HDPE, M DPE and LDPE, polyethylene terepthalate polyester (PET), polyeretherketone (PEEK) and similar polymers having low coefficients of friction.

As described previously and as alternatively depicted in FIG. 4C the entire distal end 416 of the venous anchor device 400 may be left uncoated while the tubular main body is coated. Alternatively, as shown in FIG. 5, the venous anchor device 400 may have the first portion 415 coated while the second portion 417 including plurality of barbs 421 is uncoated to ensure barbs 421 are free to lie against vessel wall.

Those of skill in the art will appreciate that although it is contemplated that the venous anchor device 400 is coated there is no backflow in the venous device due to the arterial pressure of the blood flowing through it. This minimizes any leakage that may occur at the entry point of the device in the venous wall.

Venous anchor device 400 may be either self-expanding, such as so-called shape-memory materials, or non-self-expanding, such as stainless steel. In forming the exemplary venous anchor device 400, a tubular length of metal is used to cut the venous anchor device 400 and integrally form the struts and connectors of tubular main body 412 as well as barbs 421. As discussed previously, the metal material used in the exemplary venous anchor device 400 should be both resilient and capable of being heat treated to substantially set a desired shape. Preferably, the metal from which venous anchor device 400 is cut exhibits a high modulus of elasticity that is biocompatible and has superior compressibility allowing the venous anchor device 400 to be self-expandable.

One class of materials which meet these qualifications is so-called shape memory alloys. Such alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration unless constrained from so doing.

One particularly preferred shape memory alloy for use in the present method is Nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here.

Such NiTi alloys are preferred, at least in part, because they are commercially available, have a high yield strain and more is known about handling such alloys than other known shape memory alloys. NiTi alloys are also very elastic—they are said to be "superelastic" or "pseudoelastic." This elasticity will help a device of the invention return to a present expanded configuration for deployment into a blood vessel. However, any suitable self-expanding material may be used as will be appreciated by those of ordinary skill in the art.

As hereinafter described, prior to implantation the venous anchor device 400 is collapsed inside a delivery device or sheath. Upon introduction into a vessel, the distal end of the anchoring structure freely self-expands to its original dimensions. The self-expanding behavior of the venous anchor device 400 is due to the relatively high modulus of elasticity of the shape-memory material, which imparts superior spring-like properties to the venous anchor device 400.

Referring generally to FIGS. 8 through 11, the method of implanting the arterial anchor device and venous anchor device to form the anastomotic connector in accordance with the invention will now be discussed. In a technique known to those of skill in the art to gain access to a fluid passageway of a vessel, an introducer including a stylet having a micropuncture tip puncture is introduced into the patient body. The stylet is used to puncture a small access opening through a vessel wall. The stylet is then removed with the introducer remaining in position in the fluid passageway of the vessel through the vessel wall.

Referring to FIGS. 7 through 10, the delivery device 710 used to deliver and seat the anchor devices 10, 400 in accordance with the invention in a fluid passageway broadly includes a seating device 712 comprising a wire shaft portion 713 terminating in an inflatable balloon member 714 on a distal end thereof and an outer sheath 716 into which the anchor device 10, 400 is loaded. The wire shaft 712 with donut-shaped balloon member 714 is positioned within the lumen 14 of, for example, arterial anchor device 10 with the balloon member 714 extending past aperture 36 formed by flanges 72. The combination, i e. arterial anchor device 10 and wire shaft 512 with balloon, member 714 is then housed within the outer sheath 716 of the delivery device 510 for introduction into the fluid passageway. The delivery device 710 may include radiopaque markings on the outer sheath at the proximal end which extends outside the body to enable the physician to visualize the placement of the arterial anchor device 10 in accordance with the invention. The physician guides the delivery device to the fluid passageway up to the first mark on the outer shaft, which extends the distal end of the delivery device into the fluid passageway of vessel V. The sheath 716 is then retracted to a second marking to expose the balloon member 714 and flanges 22 in the vessel fluid passageway. Flanges 22 revert to an expanded position (due to the shape memory properties and by mechanical actuation) to secure the connector 10 to an inner surface (IS) of vessel wall W. Balloon member 714 is inflated and retracted against the annular flange aperture 36 by manipulating the wire shaft 713 in a proximal direction. As the balloon member contacts the flanges 22, flanges 22 are moved to seat the anchor device to an issuer surface (IS) of vessel wall W. The sheath is further retracted proximally to expose the remaining portion 518 of the arterial anchor device extending outside the vessel wall W. The tubular main body may then be bent at the distal end to an about 90 degree angle to the longitudinal axis of the distal end. Alternatively, the about 90 degree bend may be pre-set such that when the anchor device is deployed it assumes the about 90 degree configuration. The graft material 24 is then slidably coupled to the proximal end 18 of the vessel anchor 10 having a greater outer diameter to create a fluid tight seal. Those of skill in the art will appreciate; however, that arterial anchor device 10 may be integrally formed with graft material 24 or may be pre-loaded onto the graft material 24 prior to delivery in an arterial fluid passageway. Those of skill in the art will also appreciate that the anchor device may be deployed by puncturing the raft at the mid-section, wherein the graft material would be self-sealing or a surgeon would sew it closed alternatively, a valve may be built into the side of the graft material and the anchor device deployed through the valve.

Wire shaft 713 is removed from the system leaving the arterial anchor device 10 seated in the arterial vessel fluid passageway and operably coupled to graft material 24. The foregoing process is then repeated with the venous vessel anchor 400 in a venous fluid passageway to form the anastomotic connector in accordance with the invention. However, the balloon member is optionally eliminated from seating the venous device as the barbs 421 will self-expand to anchor the device against the venous wall. FIG. 3 depicts the arterial anchor device in accordance with the invention implanted in an arterial fluid passageway and FIG. 6 depicts the venous anchor device in accordance with the invention implanted in a venous fluid passageway. As illustrated, the distal portion of the venous anchor device resides within the vessel lumen with barbs 421 lying adjacent to or embedded in the venous wall as opposed to the arterial anchor device which is seated against a vessel wall.

Additionally, it may be preferable to provide the anastomotic connectors of the invention with an inner surface that is contoured to allow smooth arterial or venous blood flow into and out of the connector device. As those of ordinary skill in the art will appreciate, providing a non-thrombogenic surface minimizes the creation of recirculation or stagnation zones with high shear or dwell times that could otherwise lead to clotting.

It is also contemplated that the inner or outer surface of the anastomotic connectors of the invention be configured to deliver and release therapeutic substances such as anti-microbial agents, anti-inflammatory agents, anti-proliferative agents (e.g. taclipaxel), growth factors, stem cells, collagen and the like. Those of ordinary skill in the art will appreciate that these therapeutic agents may be coupled with the connector and/or the external or internal surface of the connector by means such as being encased or embedded in a polymeric or other biocompatible coating, applied to a textured external surface of the connector; contained within pockets of the connector on either an internal or external surface, and the like.

As will be appreciated by those of ordinary skill in the art, the same general process described herein may be followed in order to place a connector within other types of fluid passageways. Although a method of deploying an anastomotic connector having a self-expanding anchor member has been generally described herein, the method may be adapted for deploying an anastomotic connector having a non self-expanding anchor member.

Based upon the present disclosure and after viewing the exemplary embodiment of the anastomotic connector presented herein, the many advantages and benefits provided by the invention will be appreciated by those of ordinary skill in the art. One advantage is that the geometry of the anastomotic connector allows continuous and uninterrupted arterial or venous flow during use for dialysis or other applications, thereby eliminating or substantially reducing any loss of circulation to the downstream, distal extremities. Stated alternatively, the geometry of the anastomotic connectors allows "full" flow into the graft as well as "full" flow to the downstream anatomy. Thus, distal arterial flow is not "cut-off" due to the presence of the anastomotic connector. Another advantage is that the anastomotic connectors of the invention are true percutaneous devices that do not require a "cut down" as in an "open surgery" approach. The implantation method is therefore less invasive for the patient and faster for the surgeon. Yet another advantage is that the present invention allows for maturation of the distal vein in preparation for secondary AVF while avoiding a central dialysis catheter.

Although the present invention has been described with reference to preferred embodiments, those of ordinary skill in the art will recognize that changes may be made in form and detail without departing from the spirit and scope of the invention.

What is claimed is:

1. An anastomotic connector comprising:
an arterial anchor device moveable between a loaded position and a preset expanded position the arterial anchor device comprising a generally tubular arterial anchor device main body defining a lumen therewithin, the arterial anchor device main body having a metal frame structure comprising a plurality of struts and one or more connecting members and including a distal end, a mid-portion, and a proximal end, the distal end including a variable cutting pattern such that the struts and one or more connecting members at the distal end are closer together than the struts and one or more connecting members at the mid-portion and proximal end, the distal end having a stronger radial force than the proximal end, and wherein an interface between the distal end and the mid-portion of the arterial anchor device main body has a preset angle of approximately ninety degrees offset from a longitudinal axis of the arterial anchor device main body, and a plurality of laterally-spaced apart flanges positioned circumferentially around the distal end of the arterial anchor device main body in a single row, the plurality of circumferentially positioned flanges each having a first looped end and two single-wire second ends, the second ends integrally formed with the arterial anchor device main body at the distal end thereof and each of the first looped ends are separate and distinct from an adjacent looped end, the plurality of circumferentially positioned flanges movable between a loaded position and an expanded position, wherein in the expanded position the plurality of circumferentially positioned flanges are offset from the longitudinal axis of the arterial anchor device main body by an acute angle, wherein the struts of the mid-portion are sinusoidal-shaped struts including a first row, a final row and a plurality of middle rows, wherein each middle row is connected to a subsequent middle row by the one or more connecting members each of the one or more connecting members having a first portion that extends substantially radially from a mid-portion of the strut and a second portion that extends substantially axially from the first portion, the second portion of each of the one or more connecting members connected to a peak of the strut in an adjacent row;

a separate and distinct venous anchor device comprising a generally tubular venous anchor device main body having a metal frame structure defined by a plurality of rows of struts and one or more connecting members, the plurality of rows of struts having a longitudinal spacing between the plurality of rows of struts that is substantially equivalent along a length of the venous anchor device, wherein the plurality of rows of struts of the metal frame structure are a plurality of openly-formed, sinusoidal-shaped struts, each of the plurality of rows of struts connected to an adjacent row by the one or more connecting members, each of the one or more connecting members having a first portion that extends radially from a mid-portion of the strut and a second portion that extends axially from the first portion, the second portion of each of the one or more connecting members connected to a peak of the strut in an adjacent row, the venous anchor device main body including a distal end and a proximal end, the distal end including a plurality of barbs integrally formed with the venous anchor device main body that restrict expansion of a wall of a venous passageway when the venous anchor device is exposed to arterial pressure and seated therewithin, wherein the distal end has an outer diameter greater than an outer diameter of the proximal end; and a graft material in fluid engagement with the proximal end of the arterial anchor device and the proximal end of the venous anchor device.

2. The anastomotic connector of claim 1 wherein the proximal end of the arterial anchor device has an outer diameter that is larger than or equal to an outer diameter at the distal end of the arterial anchor device.

3. The anastomotic connector of claim 1 wherein the arterial anchor device includes a plurality of tines at the proximal end thereof, the tines including a first end integrally formed with the arterial anchor device main body and a second end unattached to the arterial anchor device main body and contacting the graft material in the expanded position, the first and second ends are configured to be positioned outside of a vessel.

4. The anastomotic connector of claim 3 wherein the second end of the tines extends outwardly from the arterial anchor device main body lumen at an acute angle from a longitudinal axis of the arterial anchor device main body.

5. The anastomotic connector of claim 4 wherein the tines exert a compressive force on the graft material when the graft material is disposed over the proximal end of the arterial anchor device.

6. The anastomotic connector of claim 1 wherein the anastomotic connector is formed from a shape memory material.

7. The anastomotic connector of claim 1 further comprising a fluid impermeable material.

8. The anastomotic connector of claim 7 wherein the fluid impermeable material comprises PTFE.

9. The anastomotic connector of claim 7 wherein the fluid impermeable material is configured to be deposited on the anastomotic connector by electrospinning.

10. The anastomotic connector of claim 7 wherein the fluid impermeable material is configured to be deposited on the anastomotic connector by extrusion.

11. The anastomotic connector of claim 7 wherein the fluid impermeable material is woven.

12. The anastomotic connector of claim 7 wherein the fluid impermeable material is a polymeric material.

13. The anastomotic connector of claim 7 wherein the fluid impermeable material covers an entirety of the anastomotic connector.

14. The anastomotic connector of claim 7 wherein the fluid impermeable material covers the proximal end of the venous anchor device, a mid-portion of the venous anchor device and the distal end of the venous anchor device such that the plurality of barbs remain uncoated.

15. The anastomotic connector of claim 7 wherein the fluid impermeable material only covers the mid-portion of the arterial anchor device while the plurality of circumferentially positioned flanges and the proximal end of the arterial anchor device remain uncoated.

16. The anastomotic connector of claim 1 wherein an internal diameter of the graft material is equal to or smaller than an outer diameter of the proximal end of the arterial anchor device.

17. The anastomotic connector of claim 1 wherein the barbs of the venous anchor device extend radially outwardly at an acute angle from a longitudinal axis of the tubular venous anchor device main body.

18. The anastomotic connector of claim 1 wherein the barbs are configured to penetrate a venous vessel wall to seat the venous anchor device in a venous passageway.

19. The anastomotic connector of claim 1 wherein an outer diameter of the proximal end of the venous anchor device is greater than the inner diameter of the graft material.

20. The anastomotic connector of claim 19 wherein the proximal end of the venous anchor device forms a compression fit with the graft material.

* * * * *